United States Patent [19]

Heffelfinger et al.

[11] Patent Number: 5,591,981

[45] Date of Patent: Jan. 7, 1997

[54] TUNABLE EXCITATION AND/OR TUNABLE EMISSION FLUORESCENCE IMAGING

[75] Inventors: David M. Heffelfinger, San Pablo; Franklin R. Witney, Novato, both of Calif.

[73] Assignee: Bio-Rad Laboratories, Inc., Hercules, Calif.

[21] Appl. No.: 405,468

[22] Filed: Mar. 16, 1995

[51] Int. Cl.$^6$ .................................................. G01N 21/64
[52] U.S. Cl. ................................. 250/458.1; 250/459.1
[58] Field of Search ........................... 250/458.1, 459.1, 250/461.1, 461.2; 356/317, 318, 417

[56] References Cited

U.S. PATENT DOCUMENTS

| | | | |
|---|---|---|---|
| 4,786,170 | 11/1988 | Groebler | 356/417 |
| 4,877,966 | 10/1989 | Tomei et al. | 250/458.1 |
| 4,935,875 | 6/1990 | Shah et al. | 356/319 |
| 5,039,219 | 8/1991 | James et al. | 250/458.1 |
| 5,127,730 | 7/1992 | Brelje et al. | 250/458.1 |
| 5,377,003 | 12/1994 | Lewis et al. | 250/458.1 |
| 5,381,016 | 1/1995 | Moriya | 250/459.1 |
| 5,422,719 | 6/1995 | Goldstein | 356/318 |

FOREIGN PATENT DOCUMENTS 281945  12/1986  Japan ..................... 356/317

OTHER PUBLICATIONS

Bio-Rad Laboratories Proposal—Title: Molecular Cytogenetics Using the Genescope: An Ultrafast, Multicolor system for Automated FISH Analysis. Announcement No. 94–05, submitted Jul. 5, 1994, proposed start date Oct. 1, 1994. Advanced Technology Program Proposal.

Sales Literature on Holographic Notch and Supernotch Filters, Kaiser Optical Systems, Inc., 1992.

David M. Rust, *Etalon Filters* (Oct. 1994) 33(10) Optical Engineering 3342.

Marc Solioz, *Video Imaging of Ethidium Bromide–Stained DNA Gels with Surface UV Illumination* (1994) 16(6) BioTechniques 1130–1133.

Sales Literature on Spectral Bio–Imaging Systems, Spectral Diagnostics, Inc., Nov. 1994.

Aron T. Timperman et al., *Wavelength–Resolved Fluorescence Detection in Capillary Electrophoresis* (Jan. 1, 1995) 67(1) Analytical Chemistry 139–144.

Sales Literature on FMBIO 100 Fluorescent Imaging Device, Hitachi Software Engineering America, Ltd., 1993.

Sales Literature on Model 373A DNA Sequencing System, Applied Biosystems, undated.

Leroy E. Hood et al., *Automated DNA Sequencing and Analysis of the Human Genome*, (1987) 1 Genomics 201–212.

K. B. Bechtol et al., *Using Dyes and Filters in a Fluorescent Imaging System* (Dec. 1994) American Biotechnology Laboratory 8–10.

Sales Literature for a Digital Imaging Spectrophotomer, KAIROS, Inc., Nov. 1994.

Christopher L. Stevenson et al., *Synchronous Luminescence: A New Detection Technique for Multiple Fluorescent Probes Used for DNA Sequencing* (Jun. 1994) 16(6) BioTechniques 1104–1106.

Sales Literature on Tunable Filters, Cambridge Research Instrumentation, Inc. undated.

*Primary Examiner*—Carolyn E. Fields
*Attorney, Agent, or Firm*—David G. Beck; Townsend and Townsend and Crew

[57] ABSTRACT

A method and apparatus to detect fluorescence from a sample is provided. The optical system allows the user to continuously tune the wavelengths and bandwidths of the excitation source and the emission detection system. A peaking function automatically peaks the detected fluorescent signal by fine tuning the excitation and emission detection systems. A look-up table allows the fluorescent signal for a specific wavelength to be corrected for the wavelength dependence of the optical train. In one embodiment of the system the sample is simultaneously irradiated in more than one wavelength band, each wavelength band being independently tunable.

25 Claims, 5 Drawing Sheets

TUNABLE EXCITATION AND/OR TUNABLE EMISSION FLUORESCENCE IMAGING

BACKGROUND OF THE INVENTION

The present invention relates generally to fluorescence imaging systems and, more particularly, to a method and apparatus for fluorescence imaging in which the excitation wavelength or the emission detection wavelength or both are continuously tunable.

In the biotechnical field, fluorescent dyes are routinely used as sensitive, non-isotopic labels. These labels are used to identify and locate a variety of cell structures, ranging from malignant tumors to specific chromosomes in a DNA sequence. A variety of devices have been designed to read fluorescent-labeled samples.

In general, a device designed to read and/or image a fluorescent-labeled sample requires at least one light source emitting at one or more excitation wavelengths and means for detecting one or more fluorescent wavelengths.

In U.S. Pat. No. 5,290,419, a multi-color fluorescence analyzer is described which irradiates a sample with two or more excitation sources operating on a time-shared basis. Band pass filters, image splitting prisms, band cutoff filters, wavelength dispersion prisms and dichroic mirrors are use to selectively detect specific emission wavelengths.

In U.S. Pat. No. 5,213,673, a multi-colored electrophoresis pattern reading apparatus is described which irradiates a sample with one or more light sources. The light sources can either be used individually or combined into a single source. Optical filters are used to separate the fluorescence resulting from the irradiation of the sample into a plurality of fluorescence wavelengths.

In U.S. Pat. No. 5,190,632, a multi-colored electrophoresis pattern reading apparatus is described in which one or more light sources are used to generate a mixture of light capable of exciting two or more fluorescent substances. Both optical filters and diffraction gratings are used to separate the fluorescence by wavelength.

In U.S. Pat. No. 5,062,942, a fluorescence detection apparatus is described in which a fluorescent light image is separated into a plurality of virtual images. Bandpass filters are used to separate the virtual images by wavelength.

In an article by Cothren et al. entitled "Gastrointestinal Tissue Diagnosis by Laser-Induced Fluorescence Spectroscopy at Endoscopy," *Gastrointestinal Endoscopy* 36 (2) (1990) 105–111, the authors describe an endoscopic system which is used to study autofluorescence from living tissue. The excitation source is monochromatic with a wavelength of 370 nanometers. Optical fibers are used to collect the fluorescence emitted by the irradiated tissue. Emission spectra are collected from 350 to 700 nanometers using an imaging spectrograph coupled to a gated optical multichannel analyzer. A similar autofluorescence system was described by Andersson et al. in "Autofluorescence of Various Rodent Tissues and Human Skin Tumour Samples," *Lasers in Medical Science* 2 (41) (1987) 41–49.

The above fluorescence analyzers suffer from a number of performance disadvantages. For example, all of the systems have a very limited selection of excitation wavelengths; none of them give the user the ability to specify any particular excitation wavelength. Thus these systems do not allow the user to optimize the excitation of the fluorescent label. Furthermore, the prior art systems generally detect fluorescence in discrete wavelength bands as opposed to being continuously tunable over the detection wavelengths of interest. Without the ability to continuously tune the excitation and emission detection wavelengths, the user is not able to peak the fluorescent response.

The lack of continuous tunability of the detection wavelengths in the prior art fluorescence analyzers is especially problematic in those instances in which the chosen fluorescent labels undergo spectral shifts due to external environmental effects. For example, some fluorescent probes exhibit sensitivity to solvent polarity, solvent in this context including the interior regions of various biomolecular structures (e.g., cells, membranes, proteins, etc.). This phenomena is commonly observed in fluorescent probes which have large excited-state dipole moments. Another commonly observed cause of fluorescence spectral shifts is the pH sensitivity of many fluorescent labels. Generally, pH sensitivity is the result of a reconfiguration in the probe's $\pi$-electron system.

From the foregoing, it is apparent that a fluorescence analyzer is desired which is continuously tunable over the excitation and emission detection wavelengths.

SUMMARY OF THE INVENTION

The present invention provides a continuously tunable fluorescence detection apparatus in combination with a look-up table and/or an output signal peaking system. The tunability of the apparatus resides in the ability to tune the irradiation subassembly and/or the emissions detection subassembly to any wavelength within a continuum of wavelengths.

The tuning sections of the irradiation subassembly and the emissions detection subassembly can utilize either dispersive elements or filters. Examples of the former are prisms and gratings. Examples of the latter are short pass filters, long pass filters, notch filters, variable filters, acousto-optic filters, polarization filters, interference filters based on continuously varying film thickness, Fabrey-Perot etalon filters, tunable liquid crystal filters, and common path interferometers.

In one embodiment of the invention, the look-up table determines the optimum irradiation wavelength, emissions detection wavelength, and the associated bandwidths of each based upon application data provided by the user. Application data includes information such as the dye/stain/fluorochrome to be used as well as the intended sample support or separation matrix. In another embodiment of the invention, the look-up table contains information about the wavelength dependence of each of the elements within the apparatus. Using this information the user can compensate for any wavelength variations in the apparatus.

Although both the excitation and the emission wavelengths are well known for many fluorescent dyes, stains, and fluorochromes, various factors can result in a spectral shift of these wavelengths. In the present invention the user can compensate for these spectral shifts by tuning the irradiation subassembly and/or the emissions detection subassembly, thereby peaking the system's performance.

A fluorescence detection apparatus according to a preferred embodiment of the present invention uses a xenon lamp emitting from approximately 300 nanometers to approximately 700 nanometers. To cover a larger range of wavelengths, multiple sources can be used. A filter wheel is used in conjunction with a dispersive element to enable the user to tune the wavelength of the radiation impinging on the sample to any wavelength within the operating band of the source. A slit is used to adjust the bandwidth of the excitation radiation. Fluorescence emitted from the irradiated sample is imaged onto a CCD detector array after passing through a tuning section comprised of a filter wheel and a SAGNAC interferometer. In this embodiment the user can either set all of the operating parameters of the system manually or allow the system to automatically set the parameters based upon the user's selection of a specific fluorescent dye or probe. After choosing the initial operating parameters the user can either operate the system in this form or peak the detected fluorescent signal by varying the wavelengths and bandwidths of the excitation source and the emission detection system. Peaking the system can either be done manually or automatically. The fluorescent signals detected at different wavelengths are automatically corrected for the wavelength dependence of each element of the optical train in the preferred embodiment.

A further understanding of the nature and advantages of the present invention may be realized by reference to the remaining portions of the specification and the drawings.

DESCRIPTION OF THE PREFERRED EMBODIMENT

Figure 1:
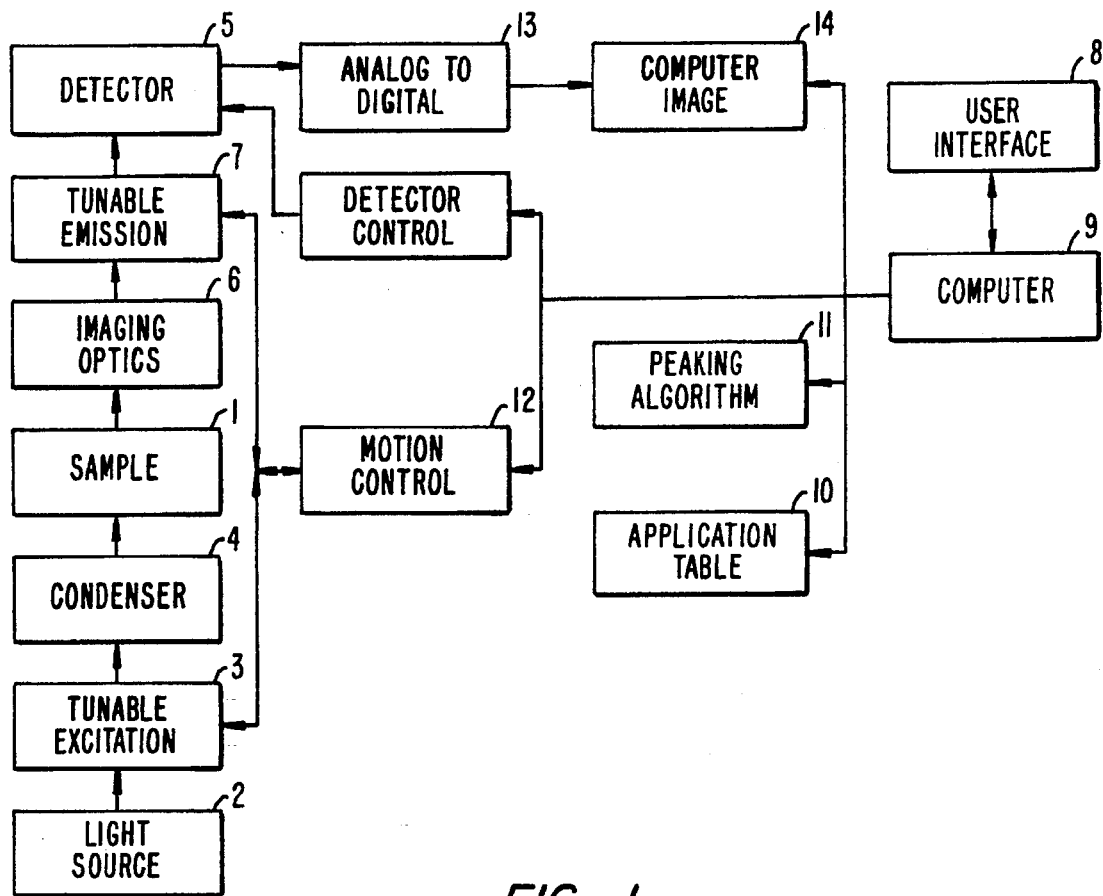
FIG. 1 is a functional block diagram of one embodiment of the invention.

FIG. 1 is a functional block diagram of one embodiment of the invention. A sample 1 may be any of a variety of materials which have been treated with a fluorescent or fluorochrome dye or probe. Sample 1 may also be a sample which exhibits autofluorescence. Light from a light source 2 passes through a tuning section 3 and condensing optics 4 prior to irradiating sample 1. The wavelength range of light source 1 in the preferred embodiment is from approximately 250 nanometers (i.e., ultraviolet radiation) to 2 micrometers (i.e., infrared radiation). Fluorescence from sample 1 is imaged onto a detector 5 after passing through imaging optics 6 and a tuning section 7.

Control of tuning sections 3 and 7 originate at a user interface 8. Interface 8 allows the user to select from a variety of instrument functions. For example, the user can select either manual or automatic control. In manual mode the user defines the operating parameters of the instrument. These parameters may include the excitation wavelength, detection wavelength, bandwidth for both the excitation and detection, and the form of the output data. In automatic mode the user specifies the fluorescent probe being used. The system, through a computer 9, then selects the appropriate instrument parameters for that particular probe by using an application table 10. Application table 10 contains a look-up table which specifies for each particular probe or dye the optimum excitation and emission wavelengths. In an alternate automatic mode the user selects certain parameters but allows the computer to peak the system using a peaking algorithm 11. For example, the user may input into interface 8 an excitation and emission wavelength. The system then fine tunes both of these parameters as well as the bandwidth of each via a controller 12 in order to optimize the performance of the system.

In the preferred embodiment the signal from detector 5 is converted to a digital signal with an A-D converter 13. On a monitor 14 an image of the sample is reconstructed. The user specifies through interface 8 what type of image is to be presented. For example, the user can select a composite image which combines the images due to a number of different wavelength probes into a single image. The user can also specify that an artificial color system is to be used in which particular probes are artificially associated with specific colors. In an alternate artificial color system the user can designate specific colors for specific emission intensities. Monitor 14 can also present a combination of the white light or "true" image of sample 1 combined with fluorescence information. Monitor 14 can also be used to present spectrographic information for a particular point on sample 1. In this mode the excitation and emission detection wavelengths are scanned allowing a spectroscopic analysis of the sample to be made. In the scanning mode, the wavelengths can either be varied over a range of wavelengths, or the system can scan over a set of specific wavelengths.

Tunable Excitation Source

Figure 2:
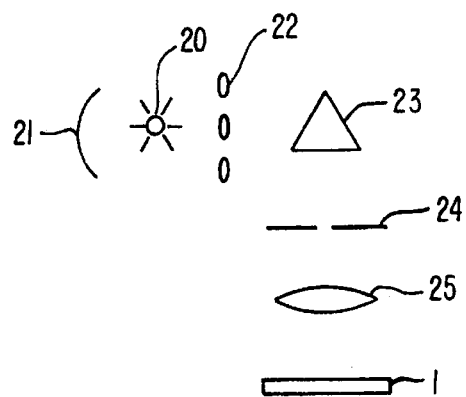
FIG. 2 is a schematic of the preferred excitation source.
Figure 3:
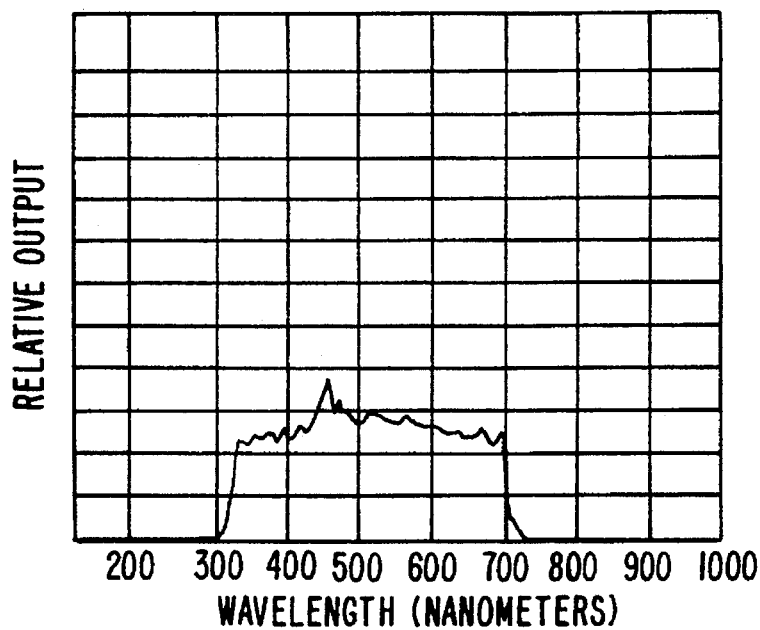
FIG. 3 is the spectral output of a xenon lamp.

FIG. 2 is a schematic of the preferred excitation source. In this embodiment a xenon arc lamp 20 is used as the source. As shown in FIG. 3, a xenon arc lamp has a relatively flat output from approximately 320 to 700 nanometers. Different wavelength bands are possible by changing the fill gas (e.g., argon instead of xenon), the temperature of the fill gas, and the material comprising the lamp envelope. A concentrator 21 is a reflective element which concentrates the output of arc lamp 20. A filter wheel 22 is used to broadly select the wavelength band of interest while a dispersive element 23 is used to fine tune the excitation source to the wavelength of interest. After the incident radiation is dispersed by element 23 it passes through variable slits 24 and condensing optics 25 before irradiating sample 1. The bandwidth of the radiation impinging on sample 1 is controlled by the width of the gap in slits 24. Elements 22–24 are controlled by stepper motors (not shown).

Figure 4:
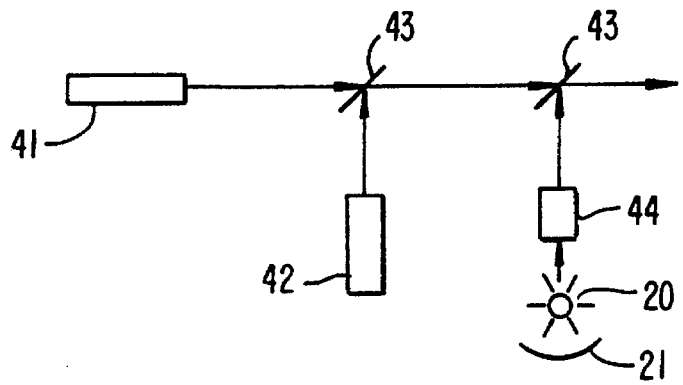
FIG. 4 illustrates one embodiment of a multi-source configuration.
Figure 5:
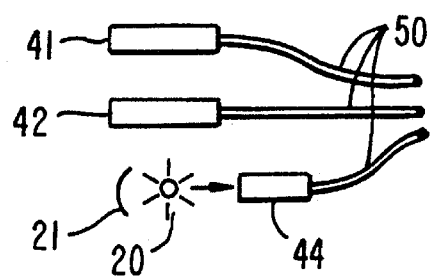
FIG. 5 illustrates a second embodiment of a multi-source configuration.

If it is desirable to have a wider selection of wavelengths than are achievable with a single xenon lamp, multiple sources can be used. FIGS. 4 and 5 illustrate two different multi-source configurations. In FIG. 4 the radiation from a laser 41 operating at a wavelength $\lambda_1$ and the radiation from a laser 42 operating at a wavelength $\lambda_2$ are combined with the broad spectrum radiation from xenon lamp 20. The individual light sources are combined using beam splitters 43. In this configuration the light from lamp 20 is sent through collimating optics 44 in order to maximize energy throughput. The light paths in FIG. 4 can be replaced with optical fibers (not shown).

In FIG. 5 radiation from sources 41, 42, and 20 are not combined into a single beam as in the configuration shown in FIG. 4. In this configuration the user (or the system in automatic mode) determines the appropriate wavelength or wavelength band. Then light from the chosen source is directed at dispersion element 23 either through manipulation of optical fibers 50 or through simple optics.

Figure 6:
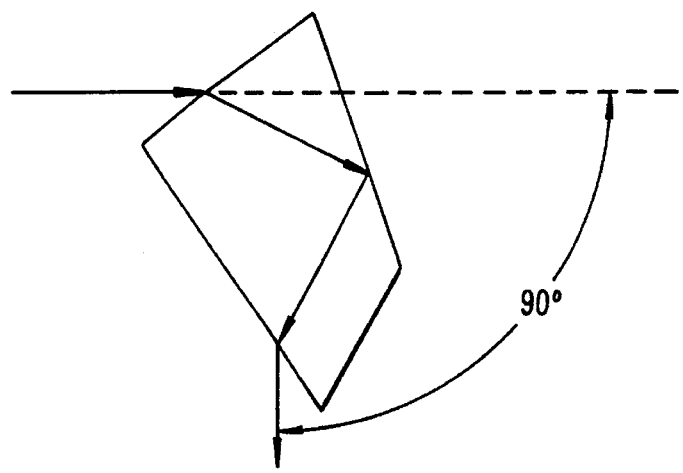
FIG. 6 illustrates a Pellin-Broca prism.

A standard prism is non-linear as a function of deviation, resulting in a rather complex optical apparatus design. In the preferred embodiment a constant deviation dispersing prism, such as the Pellin-Broca prism shown in FIG. 6, is used for dispersive element 23. In this type of prism a single monochromatic ray will pass through the prism and exit at a deviation of 90 degrees from the initial incident beam. All other wavelengths will emerge from the prism at different angles. By rotating the prism along an axis normal to the plane of the image in FIG. 6 the incoming ray will have a different angle of incidence and a different wavelength component will exit the prism at a deviation of 90 degrees. This type of prism obviously simplifies the design of the apparatus since the system can operate at a fixed angle and the wavelength can be tuned by rotating the prism.

Figure 7:
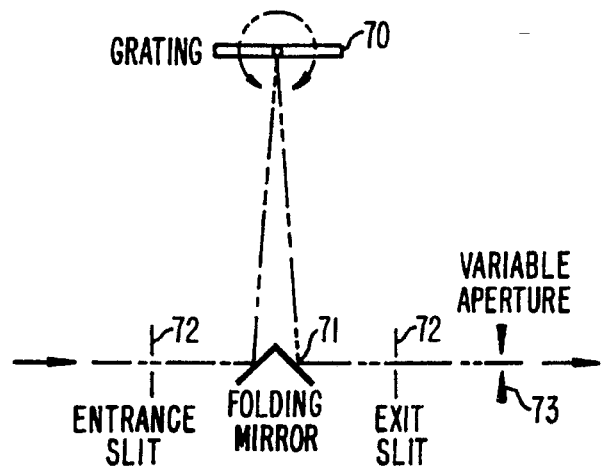
FIG. 7 illustrates a wavelength dispersive system using a grating.

A grating can also be used for dispersive element 23. FIG. 7 shows one configuration of a wavelength dispersive system comprising grating 70, folding mirror 71, entrance and exit slits 72, and aperture 73. The wavelength is tuned by rotating grating 70. The bandwidth of this system is a function of the grating groove spacing, the aperture diameter, and the distance between the aperture and the grating. In the preferred configuration multiple gratings are used which can be remotely selected depending upon the wavelength region of interest, thus insuring sufficient irradiation power throughout all the operational bands of the apparatus.

Figure 8:
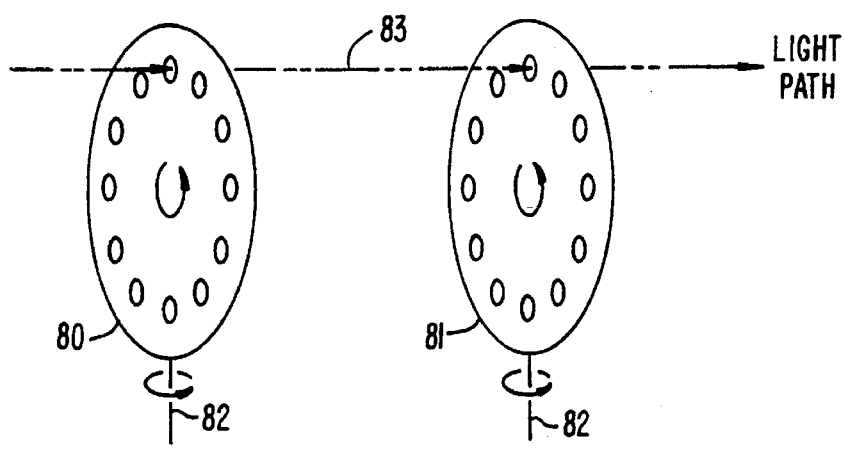
FIG. 8 illustrates a dual filter wheel approach to obtaining wavelength tunability.

Another approach to tuning the excitation source is to use optical filters. In FIG. 8 a filter wheel 80 contains a series of filters with a short pass edge while a filter wheel 81 contains a series of filters with a long pass edge. Therefore both the wavelength as well as the bandwidth is determined by the choice of filters. For example, by selecting a short pass filter of 450 nanometers and a long pass filter of 470 nanometers a 20 nanometer band centered at 460 nanometers is selected. In order to insure that the wavelength is continuously tunable, filter wheels 80 and 81 not only rotate to allow the selection of a particular filter, but they also can be rotated about an axis 82. This results in the filters being tilted with respect to optical axis 83. As the filters are tilted off-axis their wavelength characteristics gradually change.

Another approach to tuning the wavelength is to use variable filters. Circular variable filters are simply interference filters in which the film thickness varies linearly with the angular position on the substrate. An embodiment using circular variable filters would be similar in appearance to the configuration shown in FIG. 8 except that filter wheels 80 and 81 are replaced with the circular variable filters. Depending upon the position of each filter wheel and the tilt along axis 82, any wavelength can be chosen. By controlling the amount of light illuminating the filters, through the use of slits, the bandwidth can also be controlled.

In another embodiment of the invention, a Fabrey-Perot etalon tunable filter can be used to tune the excitation wavelength. In this embodiment it is generally preferable to eliminate most of the undesired wavelengths using a bandpass filter. Then the fine tuning is performing using the Fabrey-Perot system. In a variation of this system, ferroelectric liquid crystal devices can be inserted into the interference filters of the Fabrey-Perot etalon. This design is capable of high throughput as well as rapid fine tuning of the system.

Figure 9:
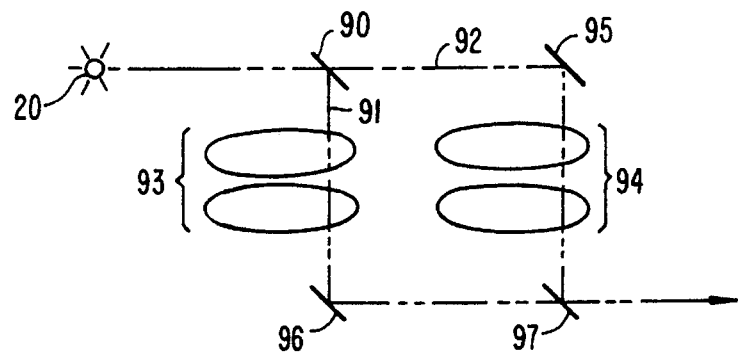
FIG. 9 is one embodiment of an excitation source capable of simultaneously irradiating the sample at more than one wavelength band.

In another embodiment of the invention, sample 1 can be illuminated simultaneously with more than one wavelength band. This allows multiple fluorescent probes to be simultaneously excited. The preferred configuration to obtain complete tunability of each wavelength band is shown in FIG. 9. Radiation from source 20 is split by a beamsplitter 90 into two paths 91 and 92 of approximately equal intensity across the entire band of interest. Path 91 passes through a wavelength tuning section, for example a series of filter wheels 93. Path 92 passes through a similar series of filter wheels 94 after being deflected by turning mirror 95. Mirror 96 and beamsplitter 97 combine paths 91 and 92 into a coaxial beam.

There are numerous variations to the configuration shown in FIG. 9. First, it is possible to split source 20 into more than two light paths, thereby allowing illumination of the sample by more than two different wavelength bands. Second, an alternate configuration is to use multiple sources, each with its own tuning section. Although more complex than the system shown in FIG. 9, this approach allows more energy within each wavelength band to impinge upon the sample. Third, a system can be designed with any of the fore-mentioned tuning sections. Fourth, it is not necessary that the individual light paths exiting each tuning section be recombined into a single path. They should, however, irradiate the same portion of the sample. Fifth, the system can be simplified by having multiple sources and having the tuning section for each source only cover a specific portion of the wavelength band. For example, the system could have three source/tuning section combinations covering 250 to 400 nanometers, 400 to 700 nanometers and 700 to 2000 nanometers, respectively. In this configuration the sources would be most efficient in the band of interest. Furthermore, the tuning sections would be simplified since simple cutoff filters could be used to eliminate radiation outside of the band of interest.

Tunable Emission Detection

In the preferred embodiment, the emission detection section of the invention allows the user to select both the wavelength and the bandwidth of the fluorescence which is to be detected. This feature allows the user to differentiate between multiple fluorescent signals as well as to eliminate noise emanating from a variety of sources such as background illumination and scattered radiation from the excitation source.

Figure 10:
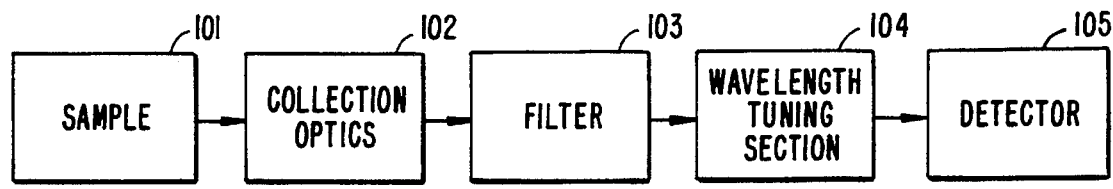
FIG. 10 shows a functional block diagram of the detection system.

FIG. 10 shows a functional block diagram of the detection system. Fluorescence from a sample 101 passes through collection optics 102 and a band pass filter wheel 103. Filter 103 is used to remove most of the undesired radiation. In the preferred embodiment filter wheel 103 is comprised of a series of filters, each with a pass band of approximately 100 nanometers. After the bulk of the undesired radiation has been removed by filter 103, the radiation passes through a wavelength tuning section 104 before impinging on a detector 105. Any of the wavelength tuning methods described for the excitation source are applicable as a means for tuning the emission detection wavelength, including both dispersive element and filtering techniques. It is also possible to simultaneously detect emissions in more than one wavelength band using techniques similar to those described above.

Figure 11:
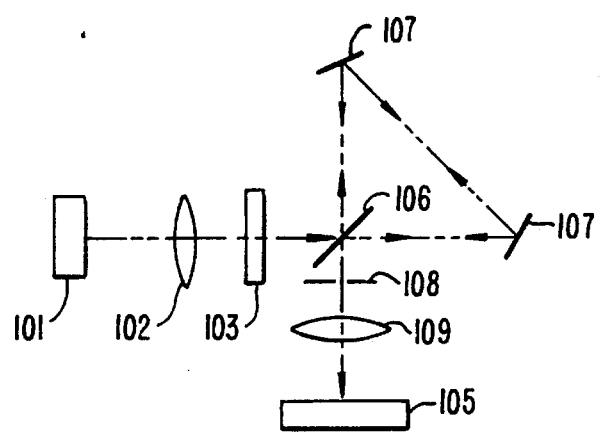
FIG. 11 shows the preferred embodiment of the detection system.

The preferred embodiment of the emission detection system is shown in FIG. 11. Fluorescence from sample 101 is collected with collection optics 102. As described above, filter wheel 103 is used to remove much of the undesired wavelength spectra. To tune the system to a specific wavelength a SAGNAC interferometer is used, the interferometer being comprised of a beam splitter 106 and turning mirrors 107. Wavelength selection is accomplished by controlling the optical path difference of the interferometer. Adjustable slit 108 controls the bandwidth. Optics 109 focus the selected emission onto detector 105. If desired, the output of detector 105 can be fourier transformed using computer 9.

Detector

Figure 12:
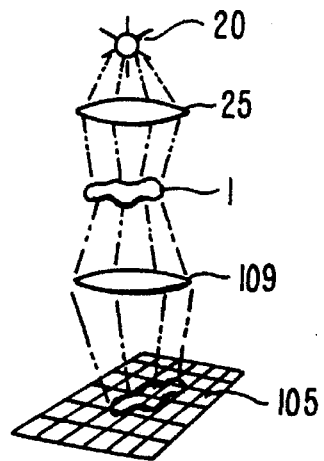
FIG. 12 shows a functional block diagram of one embodiment of the detection system.

In the preferred embodiment detector 105 is a charge coupled device (CCD) array. FIG. 12 illustrates that in this embodiment sample 1 is irradiated by source 20, the source radiation first being focussed by optics 25. The emissions from sample 1 are collected and focussed by optics 109 onto detector array 105. FIG. 12 does not illustrate any of the system's wavelength tuning capabilities. In this embodiment there is a one-to-one correspondence between the sample and the image detected by detector 105. Thus a first portion of sample 1 is imaged onto a first pixel; a second portion of sample 1 is imaged onto a second pixel, etc.

Figure 13:
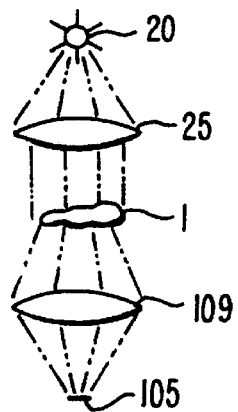
FIG. 13 shows an alternate embodiment of the detection system.

FIG. 13 shows an alternate embodiment of the detection system. In this embodiment optics 109 focus the emission from a first portion of sample 1 onto a single detector 105. Detector 105 may be a CCD, a photomultiplier tube, or any other detector which is sensitive to the wavelengths of interest. By raster scanning either focussing optics 109 or sample 1, different portions of sample 1 are serially focussed onto detector 105. Computer 9 then reconstructs an image of sample 1 which can be displayed on monitor 14.

Figure 14:
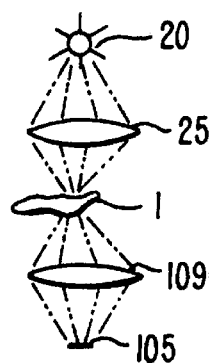
FIG. 14 shows a third embodiment of the detection system.

FIG. 14 shows a third embodiment of the detection system. In this embodiment radiation from source 20 is focussed by optics 25 onto a small portion of sample 1. Emitted radiation due to fluorescence of this portion of sample 1 is then captured and focussed by optics 109 onto detector 105. Sample 1 is raster scanned, thus allowing an entire image to be serially captured and recorded. This embodiment is especially beneficial when weak probes are used, since both the excitation radiation and the emitted fluorescence are focussed.

Look-Up Table

Look-up table 10 (FIG. 1) provides a number of functions. First, table 10 can instruct the user as to the optimum system operating parameters (i.e., excitation and emission wavelengths, excitation and emission bandwidths, etc.) for a specific experimental configuration (i.e., particular probe or dye, particular separation matrix or sample support, etc.). Second, table 10 in combination with computer 9 can be used to compensate for variations in the system. For example, the user may want to distinguish between the quantities of two different fluorescing substances within the sample. The user would most likely be in error to rely simply on the relative intensities of these two different substances. This is because each element of the optical train, from the source to the detector, is likely to exhibit some degree of wavelength dependence. All of this variational information can be programmed into the look-up table. Then, if desired, the system can automatically correct the final image for these variations.

Peaking

Peaking algorithm 11 (FIG. 1) works in conjunction with computer 9 to optimize the system's output. Peaking is one feature of the present invention which allows the user to compensate for the environmental sensitivity of a label, this sensitivity resulting in fluorescence spectral shifts. In practice, the user can either chose the initial settings for the excitation and emission detection wavelengths as well as the bandwidths of each, or the user can allow the system to automatically chose these settings on the basis of the selected dye or probe (relying on information contained in look-up table 10). If the user next selects through interface 8 that the signal be peaked, then the system will automatically peak the signal using algorithm 11. In the preferred embodiment algorithm 11 is a simple set of feedback loops. The signal from detector 105 is monitored while the source wavelength, the emission detection wavelength, and the bandwidth of both the source and detection system are varied around the initial settings. This peaking process can either be performed for a set number of times or the difference between the signal-to-noise measured at the previous setting and that measured for the currently "peaked" setting can be monitored with the process being automatically stopped when the difference becomes less than some predefined value.

System Output

In the preferred embodiment the user can select from a variety of output formats. First, an image of the sample can be shown on monitor 14. This image can be the result of measuring the fluorescence at a single wavelength, a combination of the measured emissions at several wavelengths, or a combination of fluorescence emissions and a simple "white light" image of the sample. Second, a "colored" version of the sample can be generated. In this version the user assigns a specific color for each emission wavelength. This is particularly useful when the wavelengths of two different probes are extremely close, thus allowing the user to easily differentiate between the two. Third, a spectrographic analysis of the sample can be generated and presented either on monitor 14 or on a separate plotter/printer. The spectrographic analysis can either be performed for the sample as a whole, or on a small portion of the sample. Fourth, the system can provide the user with any of the information which is routinely gathered during signal gathering. For example, the system could show the user the automatically chosen initial settings for a set of probes as well as the peaked values for the same probes. Fifth, the results from a current measurement can be compared to those from a previous measurement, assuming that the results from the previous measurement were not deleted from the system's memory.

As will be understood by those familiar with the art, the present invention may be embodied in other specific forms without departing from the spirit or essential characteristics thereof. For example, it is not necessary that a filter wheel be included in either the excitation or emission detection tuning sections. Accordingly, disclosure of the preferred embodiment of the invention is intended to be illustrative, but not limiting, of the scope of the invention which is set forth in the following claims.

We claim:

1. A fluorescence imaging system, comprising:

an interface allowing a user to specify a set of application parameters, said set of user specified application parameters selected from the group consisting of a dye type, a fluorochrome type, a stain type, a sample support, and a separation matrix;

a look-up table designating a set of imaging system operating parameters based on said set of application parameters, said set of imaging system operating parameters selected from the group consisting of a first primary wavelength, a second primary wavelength, a first band and a first bandwidth associated with said first primary wavelength, and a second band and a second bandwidth associated with said second primary wavelength;

an excitation source emitting radiation over a first range of wavelengths;

a first wavelength selector for selecting said first primary wavelength from said first range of wavelengths in a continuously tunable manner;

a focussing system for focussing radiation of said first primary wavelength on a sample, said radiation inducing said sample to fluoresce at at least one wavelength within a second range of wavelengths;

a second wavelength selector for selecting said second primary wavelength from said second range of wavelengths in a continuously tunable manner;

a detector capable of detecting fluorescence over said second range of wavelengths, said detector generating an output signal dependent upon the intensity of said fluorescence; and a display device for displaying an image of said sample, wherein said display device is responsive to said output signal.

2. The fluorescence imaging system of claim 1, further comprising means for selecting said bandwidth associated with said first primary wavelength.

3. The fluorescence imaging system of claim 2, wherein said means for selecting said bandwidth is an adjustable slit.

4. The fluorescence imaging system of claim 1, further comprising means for selecting said bandwidth associated with said second primary wavelength.

5. The fluorescence imaging system of claim 4, wherein said means for selecting said bandwidth is an adjustable slit.

6. The fluorescence imaging system of claim 1, wherein said excitation source is a xenon lamp.

7. The fluorescence imaging system of claim 1, wherein said excitation source comprises a first individual source and a second individual source.

8. The fluorescence imaging system of claim 7, wherein said first individual source is a xenon lamp and said second individual source is a laser.

9. The fluorescence imaging system of claim 1, wherein said detector is a CCD array.

10. The fluorescence imaging system of claim 1, wherein said detector is a photomultiplier tube.

11. The fluorescence imaging system of claim 1, further comprising means for correcting said output signal for a wavelength dependence of the imaging system.

12. The fluorescence imaging system of claim 1, further comprising a data processor, wherein said data processor monitors said output signal while varying said first and second primary wavelengths by controlling said first and second wavelength selectors, wherein said data processor designates a new first primary wavelength and a new second primary wavelength based on said output signal.

13. The fluorescence imaging system of claim 12, wherein said data processor causes said first and second wavelength selectors to select said first primary wavelength bandwidth and said second primary wavelength bandwidth.

14. The fluorescence imaging system of claim 1, wherein said first and second wavelength selectors are selected from the group consisting of prisms, diffraction gratings, short pass and long pass filters, variable filters, acousto-optic filters, polarization dependent filters, interference filters based on continuously varying film thickness, Fabrey-Perot etalon tunable filters, tunable liquid crystal filters, common path interferometers, and SAGNAC interferometers.

15. The fluorescence imaging system of claim 1, further comprising a filtering element interposed between said sample and said second wavelength selector, said filtering element selected from the group consisting of bandpass filters, notch filters, and polarization dependent filters.

16. The fluorescence imaging system of claim 1, further comprising a data processor, wherein said data processor determines a fourier transform of said output signal, said display device being responsive to said fourier transform.

17. A fluorescence imaging system, comprising:

an excitation source emitting radiation over a first range of wavelengths;

a first wavelength selector for selecting a first band of wavelengths from said first range of wavelengths in a continuously tunable manner;

a focussing system for focussing radiation of said first band of wavelengths on a sample, said radiation inducing said sample to fluoresce at at least one wavelength within a second range of wavelengths;

a second wavelength selector for selecting a second band of wavelengths from said second range of wavelengths in a continuously tunable manner;

a detector capable of detecting fluorescence over a second range of wavelengths, said detector generating an output signal dependent upon the intensity of said fluorescence;

a data processor, wherein said data processor monitors said output signal while varying said first and second primary wavelengths by controlling said first and second wavelength selectors, wherein said data processor designates a new first primary wavelength and a new second primary wavelength based on said output signal; and a display device for displaying an image of said sample, wherein said display device is responsive to a peaked output signal.

18. A fluorescence imaging system, comprising:

an interface allowing a user to specify a set of application parameters, said set of user specified application parameters selected from the group consisting of a dye type, a fluorochrome type, a stain type, a sample support, and a separation matrix;

a look-up table designating a set of imaging system operating parameters based on said set of application parameters, said set of imaging system operating parameters selected from the group consisting of a first plurality of wavelength bands and a second plurality of wavelength bands;

an excitation source emitting radiation over a first range of wavelengths;

a first wavelength selector for selecting said first plurality of wavelength bands from said first range of wavelengths in a continuously tunable manner;

a focussing system for simultaneously focussing radiation of said first plurality of wavelength bands on a sample, said radiation inducing said sample to fluoresce at a plurality of wavelengths within a second range of wavelengths;

a second wavelength selector for selecting said second plurality of wavelength bands from said second range of wavelengths in a continuously tunable manner;

a plurality of detectors capable of detecting fluorescence over said second range of wavelengths, said detectors generating a plurality of output signals dependent upon the intensity of said fluorescence; and a display device for displaying an image of said sample, said display device responsive to said plurality of output signals.

19. A fluorescence imaging system, comprising:

an interface allowing a user to specify a set of application parameters, said set of user specified application parameters selected from the group consisting of a dye type, a fluorochrome type, a stain type, a sample support, and a separation matrix;

a look-up table designating a set of imaging system operating parameters based on said set of application parameters, said set of imaging system operating parameters selected from the group consisting of a first primary wavelength, a second primary wavelength, a first band and a first bandwidth associated with said first primary wavelength, and a second band and a second bandwidth associated with said second primary wavelength;

an excitation source emitting radiation over a first range of wavelengths;

a first wavelength selector for selecting a first plurality of wavelength bands from said first range of wavelengths in a continuously tunable manner;

a focussing system for focussing radiation of said first plurality of wavelength bands on a sample, said radiation inducing said sample to fluoresce at a plurality of wavelengths within a second range of wavelengths;

a second wavelength selector for selecting a second plurality of wavelength bands from said second range of wavelengths in a continuously tunable manner;

a detector for sequentially detecting fluorescence within each band of said second plurality of bands, said detector generating an output signal for each band of said second plurality of bands, said output signals dependent upon the intensity of said fluorescence within each band of said second plurality of bands; and a display device for displaying an image of said sample, said display device responsive to said plurality of output signals.

20. A fluorescence imaging system, comprising:

an excitation source emitting radiation over a first range of wavelengths;

a first wavelength selector for selecting a first band of wavelengths from said first range of wavelengths in a continuously tunable manner;

a focussing system for focussing radiation of said first band of wavelengths on a sample, said radiation inducing said sample to fluoresce at at least one wavelength within a second range of wavelengths;

a detector capable of detecting fluorescence over a second range of wavelengths, said detector generating an output signal dependent upon the intensity of said fluorescence;

a data processor for peaking said output signal; and a display device for displaying an image of said sample, said display device responsive to said peaked output signal.

21. A fluorescence imaging system, comprising:

an excitation source emitting radiation over a first range of wavelengths;

a first wavelength selector for selecting a first primary wavelength from said first range of wavelengths in a continuously tunable manner;

a focussing system for focussing radiation of said first primary wavelength on a sample, said radiation inducing said sample to fluoresce at at least one wavelength within a second range of wavelengths;

a second wavelength selector for selecting a second primary wavelength from said second range of wavelengths in a continuously tunable manner;

a detector capable of detecting fluorescence over a second range of wavelengths, said detector generating an output signal dependent upon the intensity of said fluorescence; and a display device for forming an image responsive to said output signal.

22. The fluorescence imaging system of claim 21, wherein said image forming means is based on a scanning technique.

23. The fluorescence imaging system of claim 21, wherein said image forming means is based on a whole field collection technique with a one-to-one correspondence between said sample and said image detected by said detector.

24. A fluorescence imaging system, comprising:

an excitation source emitting radiation over a first range of wavelengths;

a focussing system for focussing radiation from said excitation source on a sample, said radiation inducing said sample to fluoresce at at least one wavelength within a second range of wavelengths;

a wavelength selector for selecting a band of wavelengths from said second range of wavelengths in a continuously tunable manner;

a detector capable of detecting fluorescence over a second range of wavelengths, said detector generating an output signal dependent upon the intensity of said fluorescence;

a data processor for peaking said output signal; and a display device for displaying an image of said sample, said display device responsive to said peaked output signal.

25. A method of imaging a fluorescent sample with a fluorescence image analyzer, comprising:

inputting a set of application parameters into a look-up table, said application parameters selected from the group consisting of dye type, fluorochrome type, stain type, sample type, and separation matrix;

receiving a set of system operating parameters from said look-up table, said operating parameters selected from the group consisting of a first primary wavelength, a second primary wavelength, a first bandwidth associated with said first primary wavelength, and a second bandwidth associated with said second primary wavelength, wherein said first primary wavelength is any wavelength within a first continuous range of wavelengths, and said second primary wavelength is any wavelength within a second continuous range of wavelengths;

activating an excitation source, wherein said excitation source emits radiation over said first continuous range of wavelengths;

selecting said first primary wavelength;

selecting said first bandwidth;

selecting said second wavelength;

selecting said second bandwidth;

irradiating a sample with radiation of said first primary wavelength, said irradiation inducing fluorescence emissions at said second primary wavelength;

focussing said fluorescence emissions onto a detector array; and forming an image of said sample from said fluorescent emissions, said image having a one-to-one correspondence with said sample.

* * * * *